(12) United States Patent
Seno (10) Patent No.: US 7,223,263 B1
(45) Date of Patent: May 29, 2007

(54) CATHETER

(75) Inventor: Hachiro Seno, Nagoya (JP)

(73) Assignee: Medi-Tech Co., Ltd., Saitama (JP)

( * ) Notice: Subject to any disclaimer, the term of this patent is extended or adjusted under 35 U.S.C. 154(b) by 0 days.

(21) Appl. No.: 10/018,637

(22) PCT Filed: Jun. 16, 2000

(86) PCT No.: PCT/JP00/03952

§ 371 (c)(1),
(2), (4) Date: Jun. 7, 2002

(87) PCT Pub. No.: WO00/76571

PCT Pub. Date: Dec. 21, 2000

(30) Foreign Application Priority Data

Jun. 16, 1999 (JP) ................... 11-170025

(51) Int. Cl.
*A61M 1/00* (2006.01)
(52) U.S. Cl. ..................... 604/541; 604/537
(58) Field of Classification Search ............... 604/43, 604/264, 523, 534, 540–544, 96.01, 102.01–102.03, 604/103.08, 29–30, 39–41
See application file for complete search history.

(56) References Cited

U.S. PATENT DOCUMENTS

| 3,945,385 A |   | 3/1976  | Sackner |
|---|---|---|---|
| 4,465,482 A | * | 8/1984  | Tittel ........................ 604/523 |
| 4,501,580 A | * | 2/1985  | Glassman ................... 604/43 |
| 4,579,554 A | * | 4/1986  | Glassman ............... 604/103.08 |
| 4,650,463 A |   | 3/1987  | LeVeen et al. |
| 4,935,004 A | * | 6/1990  | Cruz ........................... 604/29 |
| 5,129,910 A | * | 7/1992  | Phan et al. ................. 606/127 |
| 5,271,735 A | * | 12/1993 | Greenfeld et al. .......... 604/266 |
| 5,360,414 A | * | 11/1994 | Yarger ....................... 604/264 |
| 5,709,874 A | * | 1/1998  | Hanson et al. .............. 424/423 |

FOREIGN PATENT DOCUMENTS

| DE | 296 20 135 U1 | 2/1997 |
|---|---|---|
| EP | 284365 | 9/1988 |
| FR | 2 240 026 A | 3/1975 |
| FR | 2248057 | 5/1975 |
| JP | 48-34640 | 10/1973 |
| JP | 48-34649 | 10/1973 |
| JP | 8-206219 | 8/1996 |
| JP | 8-266616 | 10/1996 |
| WO | WO 92/04071 | 3/1992 |

OTHER PUBLICATIONS

Supplemental Search Report for EP 00 93 7280 completed on Apr. 20, 2006.

* cited by examiner

*Primary Examiner*—LoAn H. Thanh
(74) *Attorney, Agent, or Firm*—Knobbe, Martens, Olson & Bear, LLP (57) ABSTRACT

A catheter constituted of a single-pipe tube, and provided with a tip end portion (10) implanted in an abdominal cavity and a projection portion (12) projecting outward from the outer wall of the abdomen. A pair of cuffs (16, 18) are attached to the projection portion (12) and a reinforcing tube (14). Side holes (20) are drilled in the tip end portion (10), and each side hole is allowed to communicate with each other along the axial direction of the single-pipe tube by means of a groove (22) formed on the outer peripheral surface of the single-pipe tube.

14 Claims, 7 Drawing Sheets

CATHETER

TECHNICAL FIELD

This application is the U.S. National Phase under 35 U.S.C. §371 of International Application PCT/JP00/03952, filed Jun. 16, 2000, which claims priority to Japanese patent application Ser. No. 11/170,025, filed Jun. 16, 1999. The International Application was not published under PCT Article 21(2) in English.

The present invention relates to a catheter and, in particular, to a catheter suitable for discharging humor or injecting a medical fluid during cerebral surgery or thoracic surgery, and a catheter suitable for peritoneal perfusion dialysis, particularly continuous ambulatory peritoneal dialysis (CAPD).

BACKGROUND ART

In CAPD, a catheter made of silicone rubber having a diameter of 4 to 6 mm is implanted in an abdominal cavity of a renal insufficiency patient. A dialysate is injected into the abdominal cavity through this catheter, and dialysate that has stayed in the abdominal cavity is drained through the catheter after a few hours. In this way, a dialysis therapy is carried out.

A plurality of side holes, which are through-holes for draining, are formed at a tip end portion of the catheter. The catheter is implanted such that the tip end portion is positioned at a Douglas' pouch of the abdominal cavity. As the catheter is in an implanted state in the abdominal cavity for a long period of time, a membranous greater omentum that is within the abdominal cavity tangles with the tip end portion of the catheter to close side holes. Thus, there are problems in that draining from the abdominal cavity to outside becomes difficult, and consequently pain or discomfort occurs.

Japanese Patent Application Laid-Open (JP-A) No. 9-10315 discloses a catheter in which a tip end portion of an inner tube, at which tip end portion a plurality of side holes are formed, is covered with an outer tube and a bypass path is formed by a groove formed at an outer surface of the inner tube or at an inner surface of the outer tube, and thus even if side holes are closed, a cerebrospinal fluid can be evacuated via the bypass path.

However, there has been a problem in that it is difficult to manufacture a conventional catheter because the tip end portion at the catheter is formed by a double tube. Further, there is a problem that, because there is a double tube, if an outer diameter of a catheter is made small in order to reduce volume and obtain excellent implantation in an abdominal cavity, an inner diameter is reduced and draining cannot be performed well. Moreover, there could also be a problem that total draining may become impossible if the tip end portion alone is closed.

Further, JP-A No. 8-206219 describes a medical drain tube in which a plurality of grooves are formed at an outer surface of the tube in a length direction thereof, and a plurality of side holes are formed at a bottom surface of each groove.

In JP-A No. 8-206219, as the side holes are formed at the bottom surfaces of the grooves, a width of the grooves is larger than the side holes. At a time of draining-out, body tissues in vicinities of the grooves enter a little into portions of the grooves. In the state in which the body tissues have entered a little into the portions of the grooves, the side holes are not closed, and a discharge fluid flows through the grooves from the side holes into a lumen. At this time, since the tissues enter the grooves and abut corner portions of the tube that form the grooves, pain is caused to a patient. Accordingly, lightening of discomfort such as pain at the time of draining cannot be expected.

Also, the side holes are formed at the bottom surfaces of the grooves and do not communicate with each other. Thus, if draining is performed by suction by air, the side holes are closed by body tissues, draining cannot be performed through the closed side holes and as the suction proceeds, the body tissues enter into the side holes, which causes pain to the patient.

The present invention was developed in order to solve the above-described problems, and an object of the present invention is to provide a catheter of which manufacturing is easy and in which, even if volume is made small, inner diameter does not become small and draining can be performed well.

DISCLOSURE OF INVENTION

In order to accomplish the above-mentioned object, the present invention is a catheter which includes a tip end portion formed by a single-pipe tube, and a plurality of through-holes for draining, which penetrate a side wall, formed in the tip end portion. The present invention features at least one groove, which communicates a plurality of the through-holes for draining at side surfaces of the through-holes for draining and whose width is narrower than a diameter of the through-holes for draining, formed at an outer peripheral surface of the tip end portion.

This groove may be provided so as to communicate the plurality of through-holes for draining with each other in a length direction of the tip end portion, may be provided so as to communicate with each other in a peripheral direction of the tip end portion, and may be provided so as to communicate with each other in a combination of the length direction and the peripheral direction of the tip end portion.

Further, the through-holes for draining and groove may be provided at the whole of the tip end portion or provided at a part of the tip end portion.

In the present invention, the plurality of through-holes for draining are communicated with each other in the length direction of the tip end portion, the peripheral direction, or a combination of the length direction and the peripheral direction, by the groove formed at the outer peripheral surface of the tip end portion of the catheter. Thus, even if any of the communicated through-holes for draining are closed, draining can be performed from a not closed other through-hole for draining via the groove.

As described above, in the present invention, as the tip end portion of the catheter is formed by a single-pipe tube, manufacture is easy, and, even if volume of the catheter is made small, an inner diameter does not become small. Further, as the groove which communicates the through-holes for draining is provided, even if any of the through-holes for draining are closed, draining can be performed well.

With regard to peritoneal dialysis, in addition to the above-described "continuous ambulatory peritoneal dialysis" (CAPD), in which exchange of a perfusate (dialysate) is performed manually every 4 to 5 hours in the day, there is "automated peritoneal dialysis" (APD), in which exchange of a perfusate is performed mechanically, principally during sleep at night or the like. Recently, an APD proportion has been increasing.

As methods of APD, there is a gravity system, which utilizes gravity when injecting and draining, and a non-gravity system (air pressure system), which can be utilized even in Japanese-style houses and is mainly during sleep time at night. In the latter case, in a final stage of draining, bellyaches and the like, waking because of discomfort and somnipathy may occur, which is a problem. (*Easily Understood CAPD Therapy*, edited by Yasuhiko Tomino, Iyaku (Medicine and Drug) Journal Co., Ltd. pp. 111 to 112).

At present, automated peritoneal dialysis devices mainly used in Japan mainly have this non-gravity system (air pressure system). However, the present invention, based on the following theory, can lighten these bellyaches at the time of draining such that comfort during sleeping can be improved.

Draining exhibits two phases, a fast speed phase and a slow phase (*Peritoneal Dialysis* '98, pp. 165 to 168, "Problems of Automated Peritoneal Dialysis (APD) Cyclers for Underweight Babies"). In this it is understood that in a state in which a lot of dialysate remains in an abdominal cavity and intraperitoneal organs such as a greater omentum tangle little, i.e., a state in which all through-holes for draining (side holes) of a catheter operate effectively, draining speed is fast. On the other hand, it is thought that in a final stage of draining, as the dialysate remaining in the abdominal cavity reduces, the intraperitoneal organs such as an abdominal wall and the greater omentum contact the catheter. Thus, the side holes of the catheter are gradually closed. As a result, draining speed decrease. At this time, in the case of a non-gravity (air pressure) APD device, the side holes of the catheter suck the greater omentum or abdominal wall by suction. It is thought to be at this time that discomfort occurs.

In the present invention, the side holes of the catheter are connected with each other by a fairly narrow slit. Thus, even if a portion of the side holes sucks an organ such as the abdominal wall, the mechanism does not suck stronger than necessary, because of perfusion of fluid from others via the slit. This slit's width may be 0.1 mm to 0.8 mm, which even soft tissue of the intraperitoneal organs will not close.

In accordance with the present invention, as described above, since a tip end portion of a catheter is formed by a single-pipe tube, manufacture is easy. Further, as a plurality of through-holes for draining communicate with each other by a groove, an effect can be obtained that even if any of the through-holes for draining which communicate with each other by the groove are closed, draining is possible from other through-holes for draining, which are not closed, via the groove. Thus, even if the greater omentum or the like tangles during draining, easy release can be expected and thus discomfort such as pain at the time of draining can be lightened.

BEST MODE FOR CARRYING OUT THE INVENTION

Embodiments in which the present invention is applied to a catheter will be described in detail hereinafter with reference to the drawings. As shown in FIGS. 1 through 4, a catheter of a present embodiment is structured by a single-pipe tube which is made of silicone rubber with an outer diameter D (e.g., 5 mm), an inner diameter d (e.g., 2 mm to 2.5 mm), and both end portions being open. The catheter has a tip end portion 10 to be implanted in an abdominal cavity and a projection portion 12 which projects outward from an outer wall of an abdomen and connects to a bag for storing dialysate. In order to avoid positional movement within the abdominal cavity, a boundary portion between the tip end portion 10 and the projection portion 12 is covered with a short reinforcing tube 14 which is made of silicone rubber having the same hardness as the silicone rubber that structures the tip end portion or made of a silicone rubber whose hardness is high.

Figure 1:
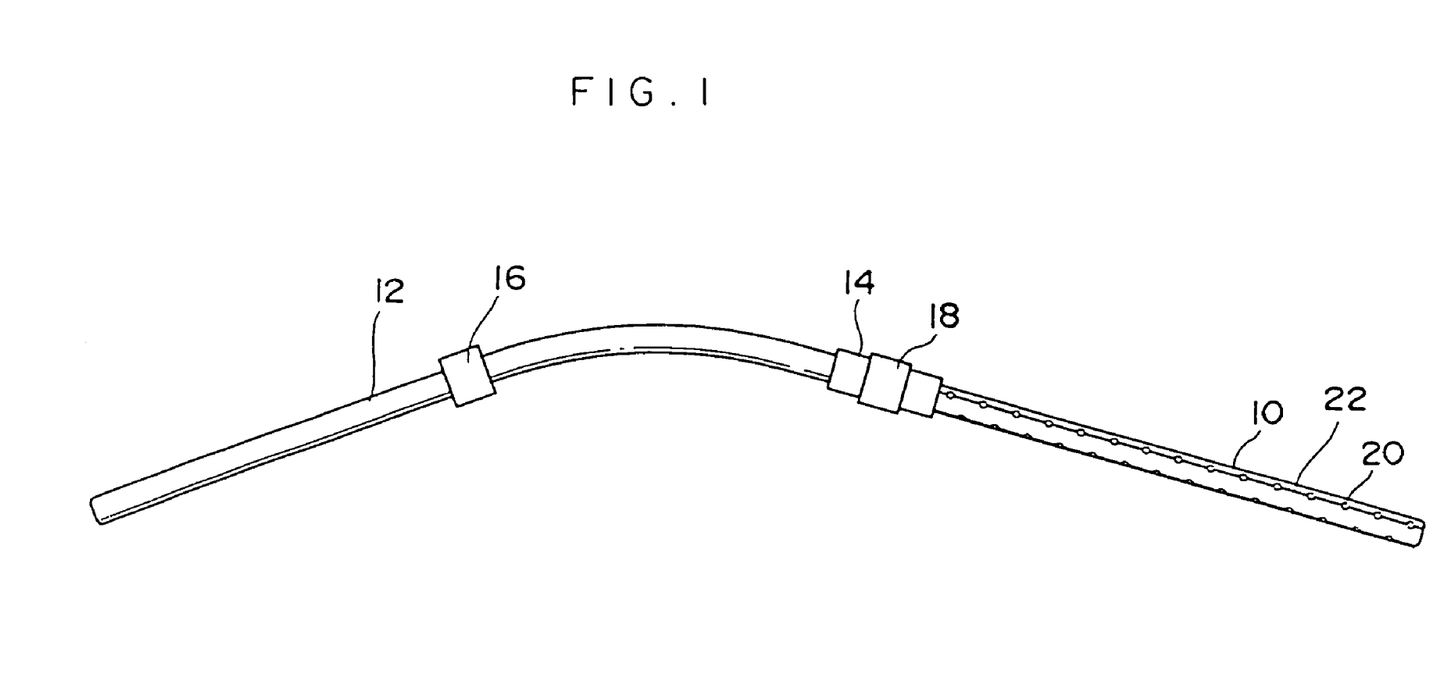
FIG. 1 is a side view of a present embodiment.

Cuffs 16 and 18 which are made of polyester nonwoven fabric in order to fix the catheter to the abdomen are attached as a pair at a substantially intermediate portion of an outer peripheral surface of the projection portion 12 and at an intermediate portion of an outer peripheral surface of the reinforcing tube 14. Incidentally, a cuff may be provided at least at the intermediate portion of the outer peripheral surface of the reinforcing tube 14, and the cuff at the substantially intermediate portion of the outer peripheral surface of the projection portion 12 may be not attached. Alternatively, two or more cuffs may be attached. The above-described reinforcing tube may be not provided at the boundary portion between the tip end portion 10 and the projection portion 12 with a cuff being attached.

Figure 2:
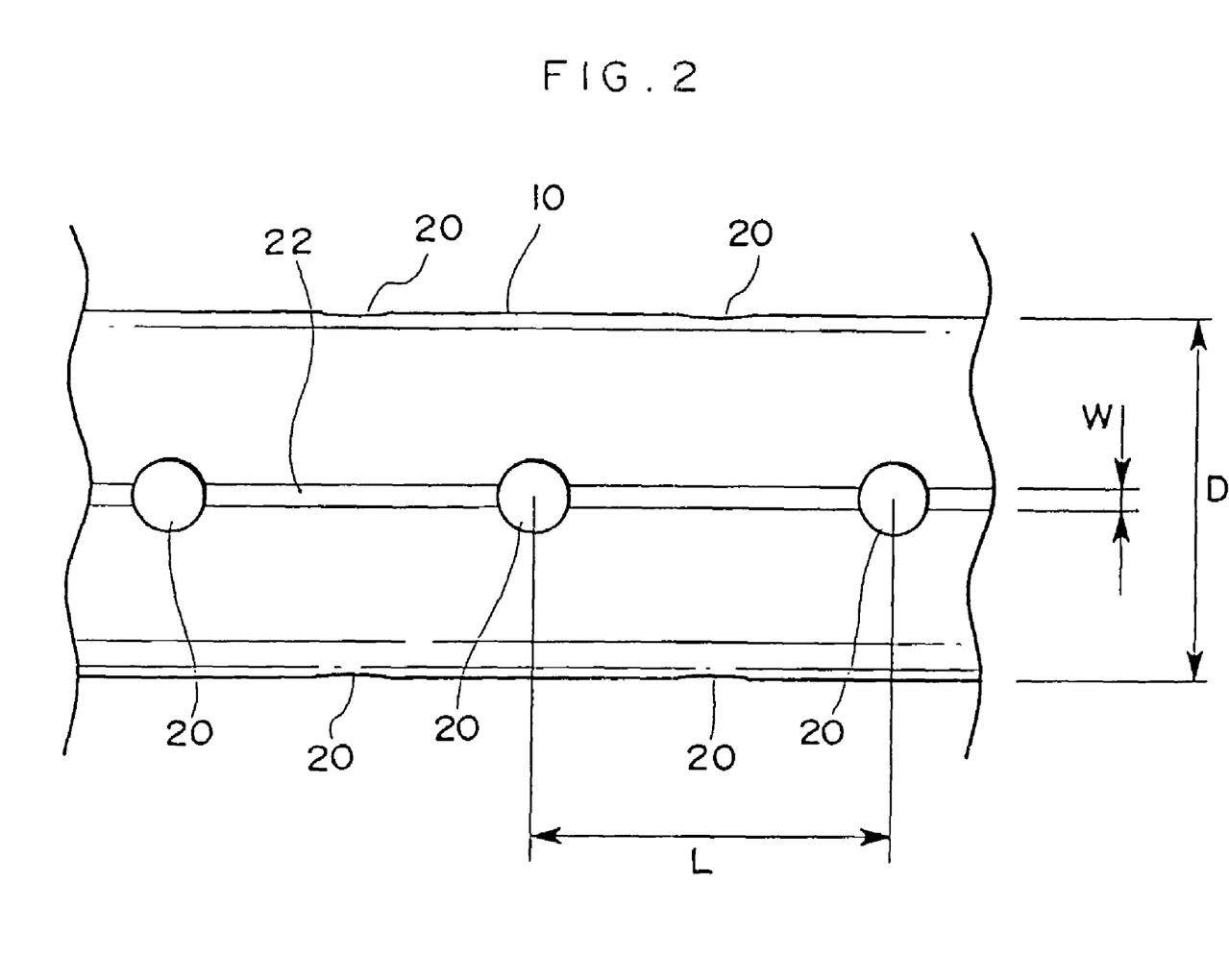
FIG. 2 is a partially enlarged view of a tip end portion of the present embodiment.
Figure 3:
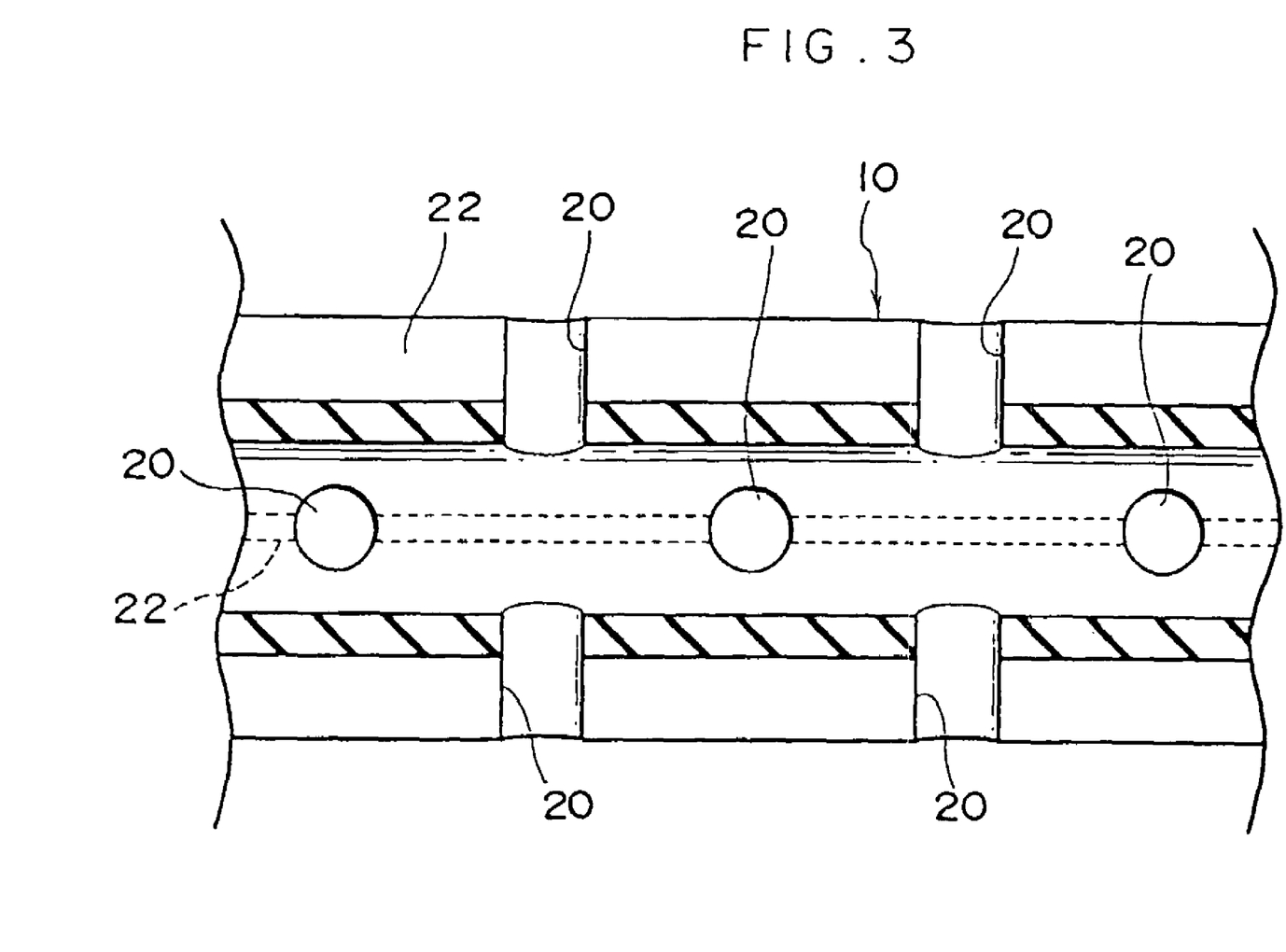
FIG. 3 is a partially enlarged horizontal sectional view of the tip end portion of the present embodiment.
Figure 4:
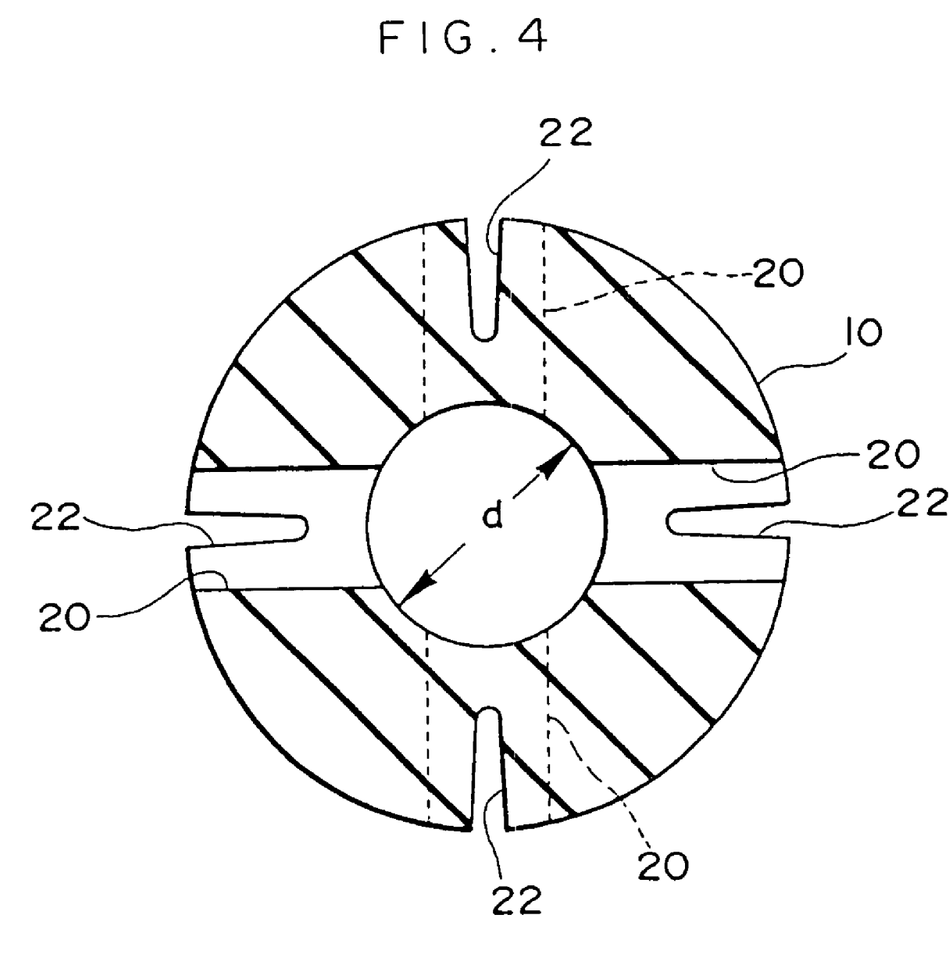
FIG. 4 is a partially enlarged vertical sectional view of the tip end portion of the present embodiment.

A plurality of side holes 20, which are through-holes for draining with a diameter of, e.g., around 1.0 mm are formed in the tip end portion 10. The plurality of side holes 20 is provided in a first two side hole rows, which are formed passing through the single-pipe tube in a diameter direction and separated along an axial direction at a predetermined interval L (e.g., 5 to 10 mm), and a second two side hole rows, which pass through such that penetration directions are shifted 90° along the circumference relative to penetration directions of the first two side hole rows and the penetration directions do not intersect. Thus, the four side hole rows respectively extend along the axial direction of the single-pipe tube. Incidentally, the penetration directions of first two side hole rows are positioned intermediately of the penetration directions of the second two side hole rows.

At each side hole row, the respective side holes are communicated, at side surfaces of the side holes 20, by a groove 22 formed on the outer peripheral surface of the single-pipe tube along the axial direction of the single-pipe tube. Each groove 22 is formed with the same size, width being narrower than diameters of the side holes 20 and depth being shallower than thickness of the single-pipe tube. The width of the grooves can be 0.1 mm to 0.8 mm, preferably 0.3 mm to 0.8 mm, and more preferably 0.3 mm. The depth of the grooves can be 0.8 mm to 1.0 mm, preferably 1.0 mm. Further, a thickness from bottom surfaces of the grooves to an inner surface of the single-pipe tube can be 0.45 mm to 0.5 mm, preferably 0.5 mm.

Figure 5:
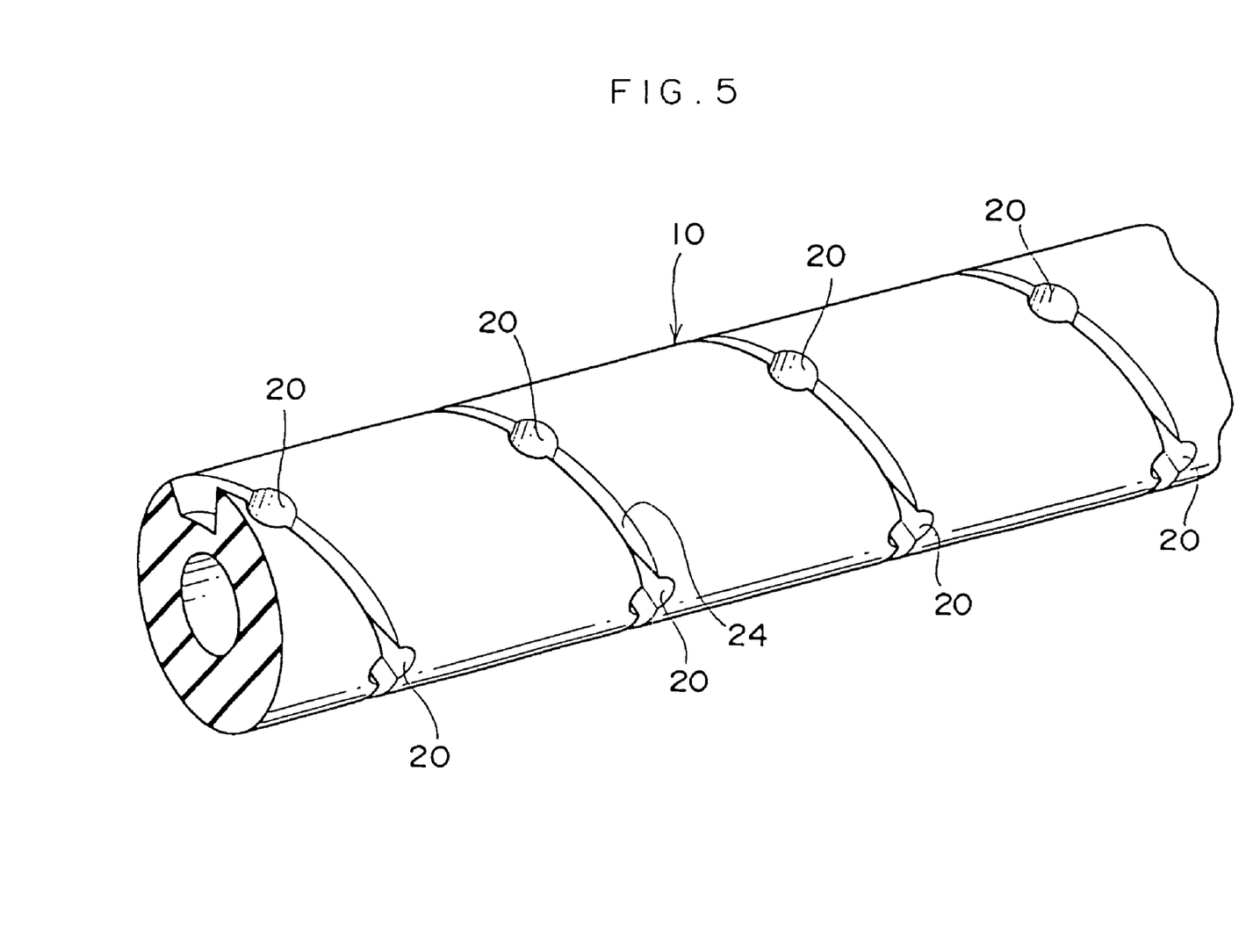
FIG. 5 is a partially enlarged view of another embodiment of the present invention.

Here, an example in which a plurality of side holes communicate in each of side hole rows has been described above. However, as shown in FIG. 5, all side holes may communicate along the axial direction of the single-pipe tube by a helical groove which extends to all rows. Alternatively, a plurality of side holes may communicate by a groove which extends along the peripheral direction of the single-pipe tube, or a combination of a length direction and peripheral direction.

Figure 6:
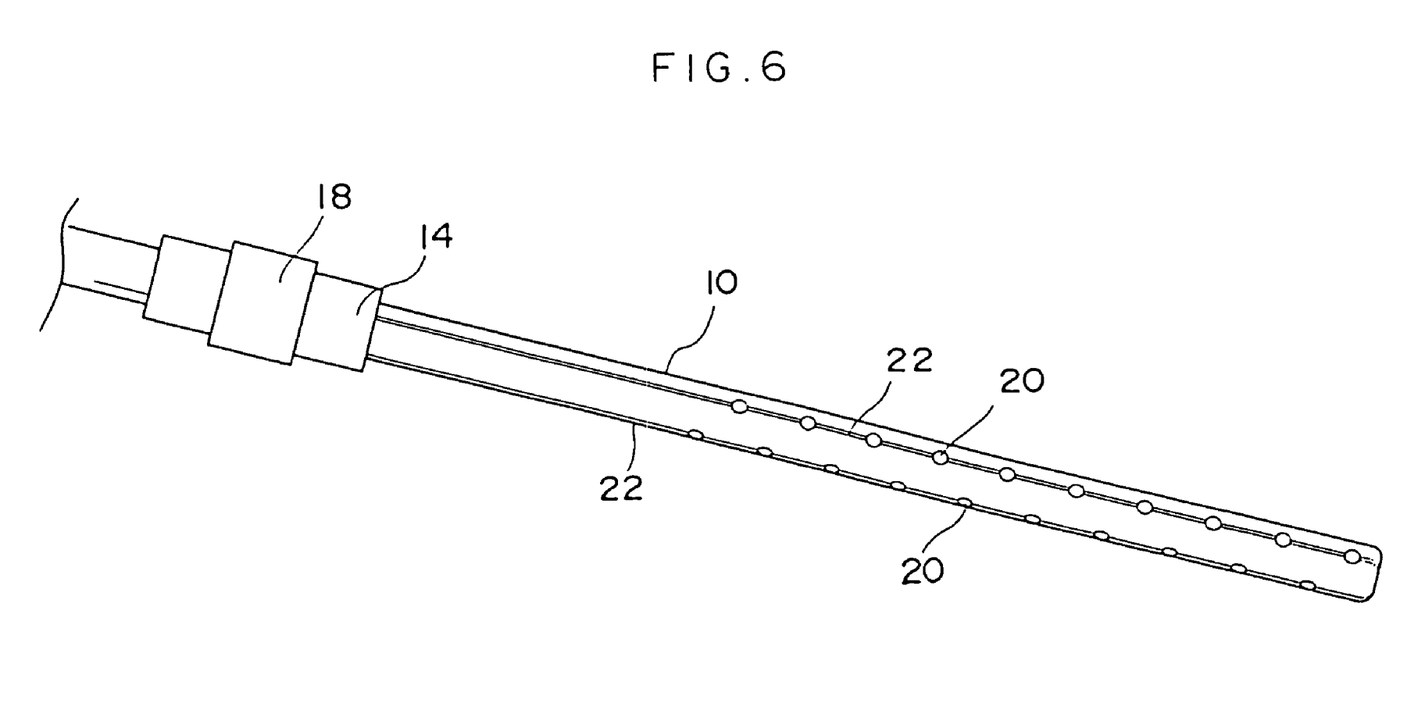
FIG. 6 is an enlarged view of a tip end portion of still another embodiment of the present invention.
Figure 7:
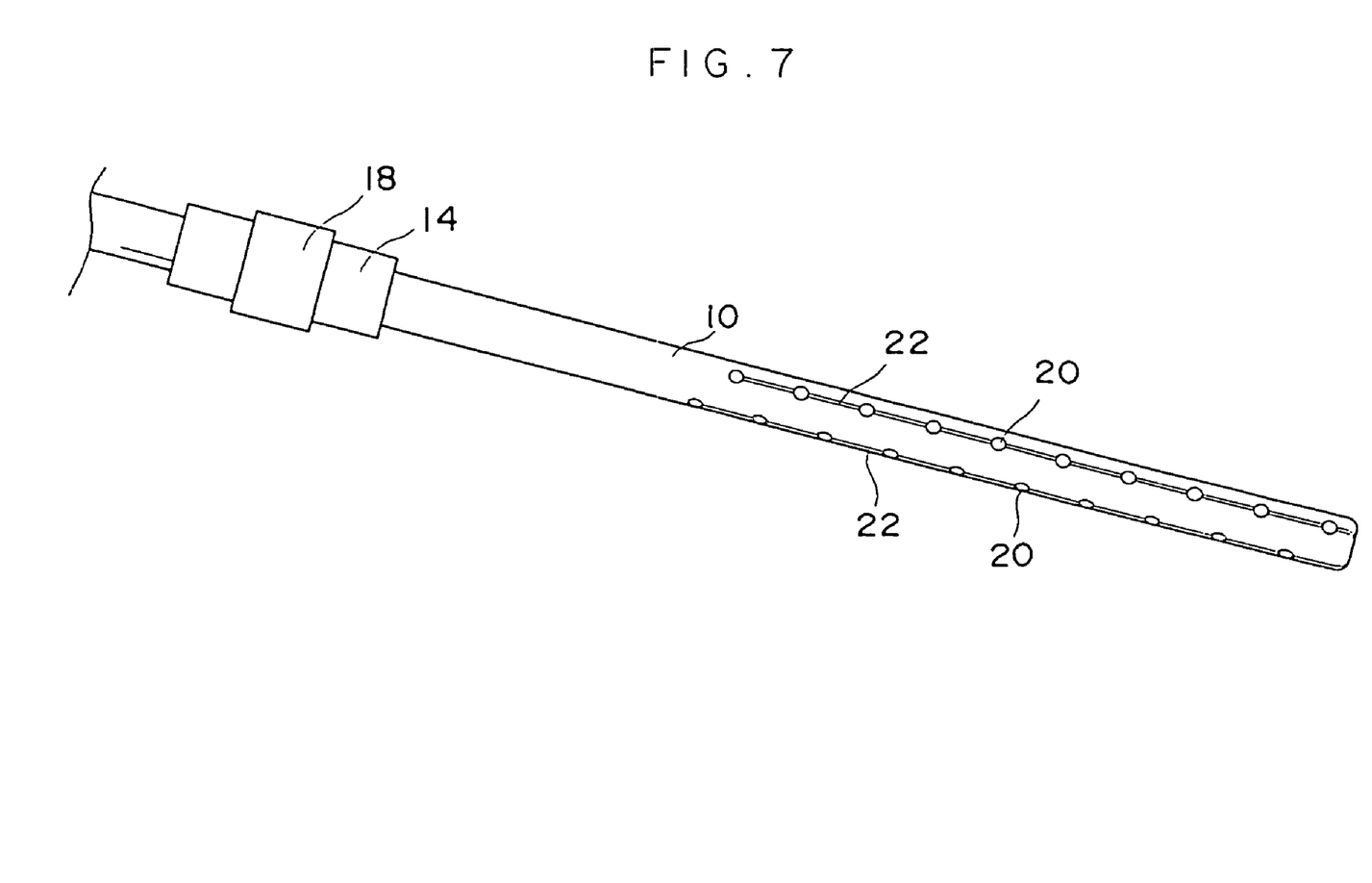
FIG. 7 is an enlarged view showing a modified example of the embodiment of FIG. 6.

Moreover, as shown in FIG. 6, side holes may be provided at a region of a predetermined range from a tip end of the tip end portion, with the grooves communicating each side hole being formed along the whole length of the tip end portion, or, as shown in FIG. 7, the side holes may be provided at the region of a predetermined range from the tip end of the tip end portion, with the grooves being provided only at a portion to communicate each side hole.

An example in which the catheter is formed by one single-pipe tube has been described above. However, the tip end portion 10 and the projection portion 12 may be formed of separate single-pipe tubes having the same diameter, with the tip end portion 10 being connected to the projection portion 12 by bonding or the like. In this case, a connecting portion of the tip end portion 10 and the projection portion 12 is preferably reinforced by the above-described reinforcing pipe.

In the present embodiments, a plurality of through-holes for draining are communicated with each other by grooves formed in an outer peripheral surface of a catheter. Thus, even if any of the through-holes for draining communicated by the grooves are closed, draining is possible from other through-holes for draining, which are not closed, via the grooves.

The invention claimed is:

1. A catheter comprising:
a tip end portion which is formed of a single-pipe tube and is adapted to be implanted in an abdominal cavity, and in which a plurality of through-hole rows are formed, the through-hole row including a plurality of through-holes for draining formed so as to penetrate a side wall of the single-pipe tube and to be separated by a predetermined interval along an axial direction of the single-pipe tube; and
a projection portion which is projected outside from an abdomen outer wall, wherein a plurality of grooves are provided at an outer peripheral surface of the tip end portion, each individual groove of the plurality of grooves communicates with the plurality of through-holes at side surfaces of said through-holes along a direction in which said through-hole row extends, said each groove is narrower than a diameter of said through-holes and is formed only at an outer peripheral surface of said tip end, a depth of each groove is 0.8 mm to 1.0 mm, and each groove is formed such that the width of the groove is narrower at the inner portion thereof than at the opening thereof, and such that the depth of the groove is greater than the width of the groove at the groove opening.

2. The catheter of claim 1, further comprising a cuff for fixing said catheter to an abdominal portion.

3. The catheter of claim 2, wherein said groove is formed along an entire length of said tip end portion.

4. The catheter of claim 3, wherein width of said groove is 0.1 mm to 0.8 mm.

5. The catheter of claim 2, wherein width of said groove is 0.1 mm to 0.8 mm.

6. The catheter of claim 1, wherein said groove is formed along an entire length of said tip end portion.

7. The catheter of claim 6, wherein width of said groove is 0.1 mm to 0.8 mm.

8. The catheter of claim 1, wherein width of said groove is 0.1 mm to 0.8 mm.

9. The catheter of claim 1, wherein said through-holes for draining are side holes.

10. The catheter of claim 1, wherein said groove is a slit which is not closed even by soft tissue of an intraperitoneal organ.

11. The catheter of claim 1, wherein the depth of each groove is 1.0 mm.

12. A catheter comprising:
a tip end portion which is formed of a single-pipe tube and is adapted to be implanted in an abdominal cavity, and in which a plurality of through-hole rows are formed, the through-hole row including a plurality of through-holes for draining formed so as to penetrate a side wall of the single-pipe tube and to be separated by a predetermined interval along an axial direction of the single-pipe tube; and
a projection portion which is projected outside from an abdomen outer wall,
wherein a plurality of grooves are provided at an outer peripheral surface of the tip end portion, each individual groove of the plurality of grooves communicates with the plurality of through-holes at side surfaces of said through-holes along a direction in which said through-hole row extends, said each groove is narrower than a diameter of said through-holes and is formed only at an outer peripheral surface of said tip end, a thickness from bottom surfaces of each groove to the inner surface of the single-pipe tube is 0.45 mm to 0.5 mm, and each groove is formed such that the width of the groove is narrower at the inner portion thereof than at the opening thereof, and such that the depth of the groove is greater than the width of the groove at the opening.

13. The catheter of claim 12, wherein the thickness from bottom surfaces of each groove to the inner surface of the single-pipe tube is 0.5 mm.

14. A catheter comprising:
a tip end portion which is formed of a single-pipe tube and is adapted to be implanted in an abdominal cavity, and in which a plurality of through-hole rows are formed, the through-hole row including a plurality of through-holes for draining formed so as to penetrate a side wall of the single-pipe tube and to be separated by a predetermined interval along an axial direction of the single-pipe tube; and
a projection portion which is projected outside from an abdomen outer wall,
wherein a plurality of grooves are provided at an outer peripheral surface of the tip end portion, each individual groove of the plurality of grooves communicates with the plurality of through-holes at side surfaces of said through-holes along a direction in which said through-hole row extends, said each groove is narrower than a diameter of said through-holes, and each groove is formed such that the width of the groove is narrower at the inner portion thereof than at the opening thereof, and such that the depth of the groove is greater than the width of the groove at the opening.

* * * * *

UNITED STATES PATENT AND TRADEMARK OFFICE
CERTIFICATE OF CORRECTION

PATENT NO.       : 7,223,263 B1
APPLICATION NO.  : 10/018637
DATED            : May 29, 2007
INVENTOR(S)      : Hachiro Seno It is certified that error appears in the above-identified patent and that said Letters Patent is hereby corrected as shown below:

On The Title Page, Item (56), under References Cited U.S. PATENT DOCUMENTS, insert -- 4,317,452  3/1982  Russo et al. --

Signed and Sealed this

Twentieth Day of November, 2007

JON W. DUDAS
*Director of the United States Patent and Trademark Office*